United States Patent
Nakano et al.

(10) Patent No.: US 9,271,878 B2
(45) Date of Patent: Mar. 1, 2016

(54) APPARATUS FOR MANUFACTURING ABSORBENT ARTICLE AND METHOD FOR MANUFACTURING ABSORBENT ARTICLE

(75) Inventors: Takumi Nakano, Kagawa (JP); Yoshihiko Matsumoto, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 301 days.

(21) Appl. No.: 14/000,336

(22) PCT Filed: Dec. 8, 2011

(86) PCT No.: PCT/JP2011/078452
§ 371 (c)(1),
(2), (4) Date: Oct. 25, 2013

(87) PCT Pub. No.: WO2012/114606
PCT Pub. Date: Aug. 30, 2012

(65) Prior Publication Data
US 2014/0054128 A1 Feb. 27, 2014

(30) Foreign Application Priority Data
Feb. 23, 2011 (JP) .................................. 2011-036995

(51) Int. Cl.
*A61F 13/15* (2006.01)
(52) U.S. Cl.
CPC ..... *A61F 13/15609* (2013.01); *A61F 13/15593* (2013.01)

(58) Field of Classification Search
CPC ..................... A61F 13/15609; A61F 13/15764
See application file for complete search history.

(56) References Cited

U.S. PATENT DOCUMENTS

| 2004/0123954 A1 | 7/2004 | Yoneoka et al. |
| 2006/0185135 A1 | 8/2006 | Yamamoto et al. |
| 2010/0078127 A1 | 4/2010 | Yamamoto et al. |

FOREIGN PATENT DOCUMENTS

| JP | 2004-155586 A | 6/2004 |
| JP | 2004-159866 A | 6/2004 |
| JP | 2010-115284 A | 5/2010 |

OTHER PUBLICATIONS

International Search Report and Written Opinion corresponding to PCT/JP2011/078452, dated Jan. 10, 2012.
Office Action mailed Feb. 17, 2015, corresponding to Japanese patent application No. 2011-036995.

*Primary Examiner* — Vishal I Patel
(74) *Attorney, Agent, or Firm* — Hauptman Ham, LLP

(57) ABSTRACT

An apparatus for manufacturing an absorbent article includes a guide member that guides an elastic member fed on a web configuring a component of the absorbent article and being conveyed in a continuous state. The guide member includes: an arm member having a tip portion that is a feeding position of the elastic member to the web, and a base portion separated from the tip portion; a first drive member that swings the arm member about the base portion of the arm member as a rotational axis; and a second drive member that performs a back and forth movement of the arm member and the first drive member along a cross direction that crosses a conveyance direction in which the web is conveyed.

6 Claims, 6 Drawing Sheets

APPARATUS FOR MANUFACTURING ABSORBENT ARTICLE AND METHOD FOR MANUFACTURING ABSORBENT ARTICLE

RELATED APPLICATIONS

The present application is a National Phase of International Application Number PCT/JP2011/078452, filed Dec. 8, 2011, and claims priority from Japanese Application Number 2011-036995, filed Feb. 23, 2011.

TECHNICAL FIELD

The present invention relates to an apparatus for manufacturing an absorbent article and a method for manufacturing the absorbent article for arranging an elastic member on a web that is conveyed in a continuous state configuring a part of component of the absorbent article, and a method for manufacturing the absorbent article.

BACKGROUND ART

Conventionally, in a step of manufacturing an absorbent article such as a disposable diaper, in order to improve the fitting in the leg hole region and the crotch region of the wearer, a method for arranging elastic members at the position corresponding to the leg hole region and the crotch region is used widely.

Specifically, according to the manufacturing step, continuous elastic members are arranged in a waveform on a continuous web configuring component of the absorbent article.

That is, by arranging elastic members in a waveform on the web on which a longitudinal direction of an absorbent article is arranged along a cross direction that crosses a conveyance direction of the web, an absorbent article having gathers corresponding to the shape of the leg hole region and the crotch region can be manufactured continuously.

Patent Literature 1 and Patent Literature 2 disclose a method for arranging elastic members in a waveform on a web that is conveyed. Specifically, by using a base portion of an arm member that is directly coupled to a rotational axis of a motor as the rotational axis, the arm member is swung in the cross direction of the web, while elastic members are fed from a tip portion of the arm member, and the elastic members are arranged in a waveform on the web. Next, by sandwiching the elastic members and the web by press rolls provided above and below the web, the elastic members supplied on the web are brought in contact and arranged on the web.

CITATION LIST

Patent Literature

[PTL 1] Japanese Unexamined Patent Application Publication No. 2004-159866 (Pages 6 through 8, FIGS. 3 and 4)
[PTL 2] Japanese Unexamined Patent Application Publication No. 2010-115284 (Pages and 6, FIGS. 3 and 4)

SUMMARY OF INVENTION

However, the aforementioned conventional method for arranging elastic members has the below-mentioned problem. That is, the arm members swing about the base portion that is connected to the rotational axis of the motor. Therefore, the movement trajectory of the feeding position of the elastic members that form the tip portion of the arm members is in the shape of an arc. Thus, the distance between the contact point where the elastic members and web contact and the feeding position changes at all times, and the feeding position and the contact point are sometimes displaced in the cross direction. For example, the distance between the feeding position and the contact point becomes longer at an end in the cross direction of the movement trajectory of the feeding position than at the center in the cross direction of the movement trajectory. Therefore, in the state when the feeding position is positioned at an end in the cross direction, the length of displacement of the feeding position and the contact point in the cross direction becomes longer. In view of the length of displacement of the feeding position and the contact point, when the tip portion of the arm members is positioned near an end in the cross direction, the tip portion of the arm members needs to be moved outer sides than the contact point where the elastic members be arranged in the cross direction. Thus, the acceleration of the arm members increases at near the end in the cross direction.

Particularly, in the case of the size of the absorbent article to be manufactured needs to be increased, for example, in the case of a disposable diaper for adults, the width of swinging of the arm members needs to be increased as compared to a disposable diaper for infants. When the width of swinging of the arm members is relatively larger, the distance between the feeding position and the contact point near the end in the cross direction becomes further longer, and the acceleration of the arm members near the end in the cross direction increases further. Thus, the arm members themselves cannot bear the acceleration and may end up being damaged.

Thus, the present invention has been achieved in view of such a situation, and an object thereof is to provide an apparatus for manufacturing an absorbent article and a method for manufacturing an absorbent article with which it is possible to handle several sizes while surely reducing the damage of an arm member.

In order to resolve the above problem, the apparatus for manufacturing absorbent articles according to the present disclosure is summarized as the apparatus for manufacturing absorbent articles having a front waistline region (front waistline region 10), a rear waistline region (rear waistline region 20), and a crotch region (crotch region 30) positioned between the front waistline region and the rear waistline region, comprising: a guide member (guide member 120) that guides an elastic member (elastic member 6) fed on a web (composite web 7) configuring a component of the absorbent article (absorbent article 1) and being conveyed in a continuous state, wherein the guide member comprises: an arm member (arm member 121) having a tip portion (tip portion 122) that is a feeding position of the elastic member to the web, and a base portion (base portion 123) separated from the tip portion; a first drive member (first drive member 125) that swings the arm member about the base portion of the arm member as a rotational axis; and a second drive member (second drive member 128) that performs a back and forth movement of the arm member and the first drive member along a cross direction that crosses a conveyance direction in which the web is conveyed.

In order to resolve the above problem, the method for manufacturing absorbent articles according to the present disclosure is summarized as the method for manufacturing absorbent articles having a front waistline region, a rear waistline region, and a crotch region positioned between the front waistline region and the rear waistline region in which an elastic member is arranged on a web configuring a component of the absorbent article and being conveyed in a continuous state, by swinging an arm member having a tip portion that is a feeding position of the elastic member to the web within a predetermined range in a cross direction that crosses a conveyance direction, comprising: a step of conveying the web in the conveyance direction; and a step of arranging the elastic member on the web by swinging the tip portion of the arm member while performing a back and forth movement of the arm member in the cross direction.

DESCRIPTION OF EMBODIMENTS

Figure 1:
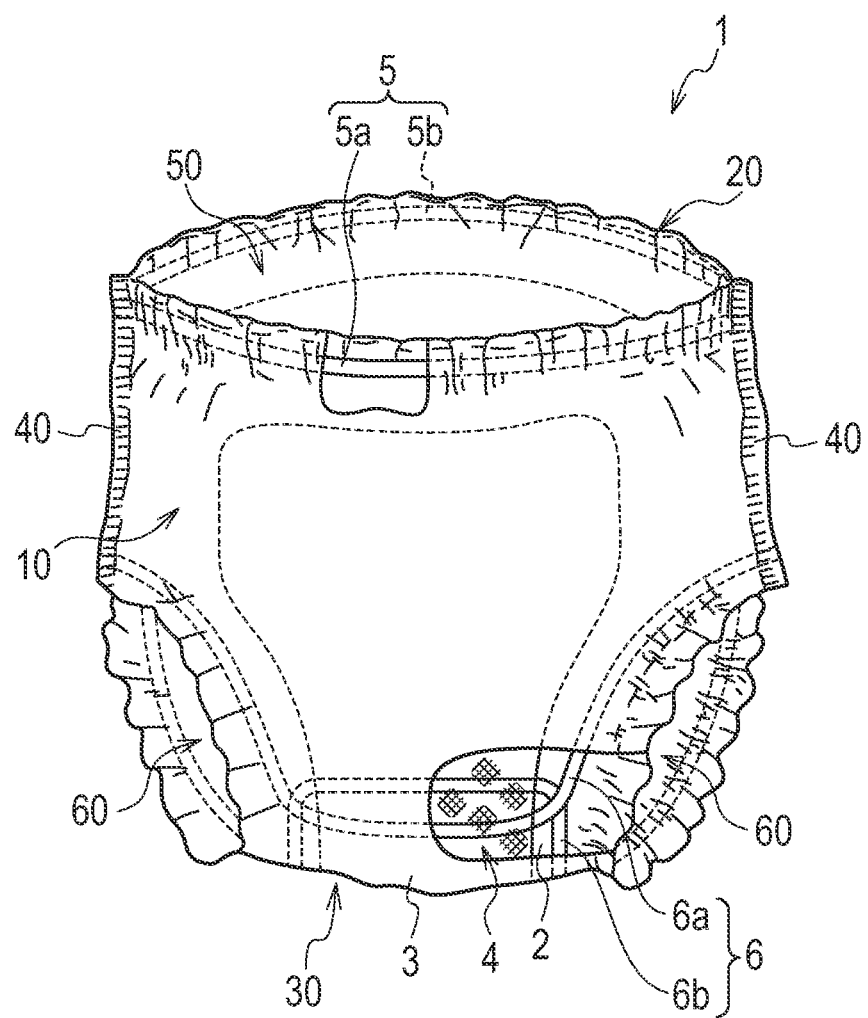
FIG. 1 is a perspective view illustrating an absorbent article according to the present embodiment.

Next, a method for manufacturing an absorbent article according to the present invention is explained with reference to drawings. Specifically, (1) Configuration of absorbent article, (2) Method for manufacturing absorbent article, (3) Configuration of elastic member mounting device, (4) Operation of elastic member mounting device, (5) Configuration of guide member, (6) Operation of guide member, and (7) Other embodiments will be explained.

In the following description of the drawings, the same or similar reference numerals are used to designate the same or similar parts. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

(1) Configuration of Absorbent Article

First of all, a configuration of an absorbent article according to the present embodiment is explained with reference to drawings. FIG. 1 is a perspective view showing the absorbent article according to the present embodiment. In the present embodiment, an absorbent article 1 is a disposable diaper for adults.

As shown in FIG. 1, the absorbent article 1 is roughly configured by: a liquid-permeable topsheet 2 that is in contact with the skin of the wearing subject (hereinafter, the wearer); a backsheet 3 provided on the outer side of the topsheet 2; and an absorber 4 that is provided between the topsheet 2 and the backsheet 3 and absorbs the excretion from the wearer.

Note that a liquid-impermeable waterproof sheet (not shown in the figure) is provided between the backsheet 3 and the absorber 4. In other words, the absorber 4 is provided between the topsheet 2 and the waterproof sheet.

A nonwoven fabric or a perforated plastic film, for example, is used in the topsheet 2. A nonwoven fabric is used in the backsheet 3. Powdered pulp or a mixture of powdered pulp or highly absorbent polymer is used in the absorber 4. A plastic film, a nonwoven fabric, or a combined sheet of a plastic film and a nonwoven fabric, for example, is used in the waterproof sheet.

The absorbent article 1 has a front waistline region 10 corresponding to the front waistline of the wearer, a rear waistline region 20 corresponding to the rear waistline of the wearer, and a crotch region 30 corresponding to the crotch of the wearer.

The front waistline region 10 and the rear waistline region 20 are formed as one part by a joint portion 40. Waist gathers 5 made of thread-shaped rubber, for example, having elasticity are provided on the circumference of the front waistline region 10 and the rear waistline region 20. The waist gathers 5 are configured from front waist gathers 5a positioned in the front waistline region 10 and rear waist gathers 5b positioned in the rear waistline region 20. A waist opening region 50 is formed between the front waist gathers 5a and the rear waist gathers 5b.

Figure 2:
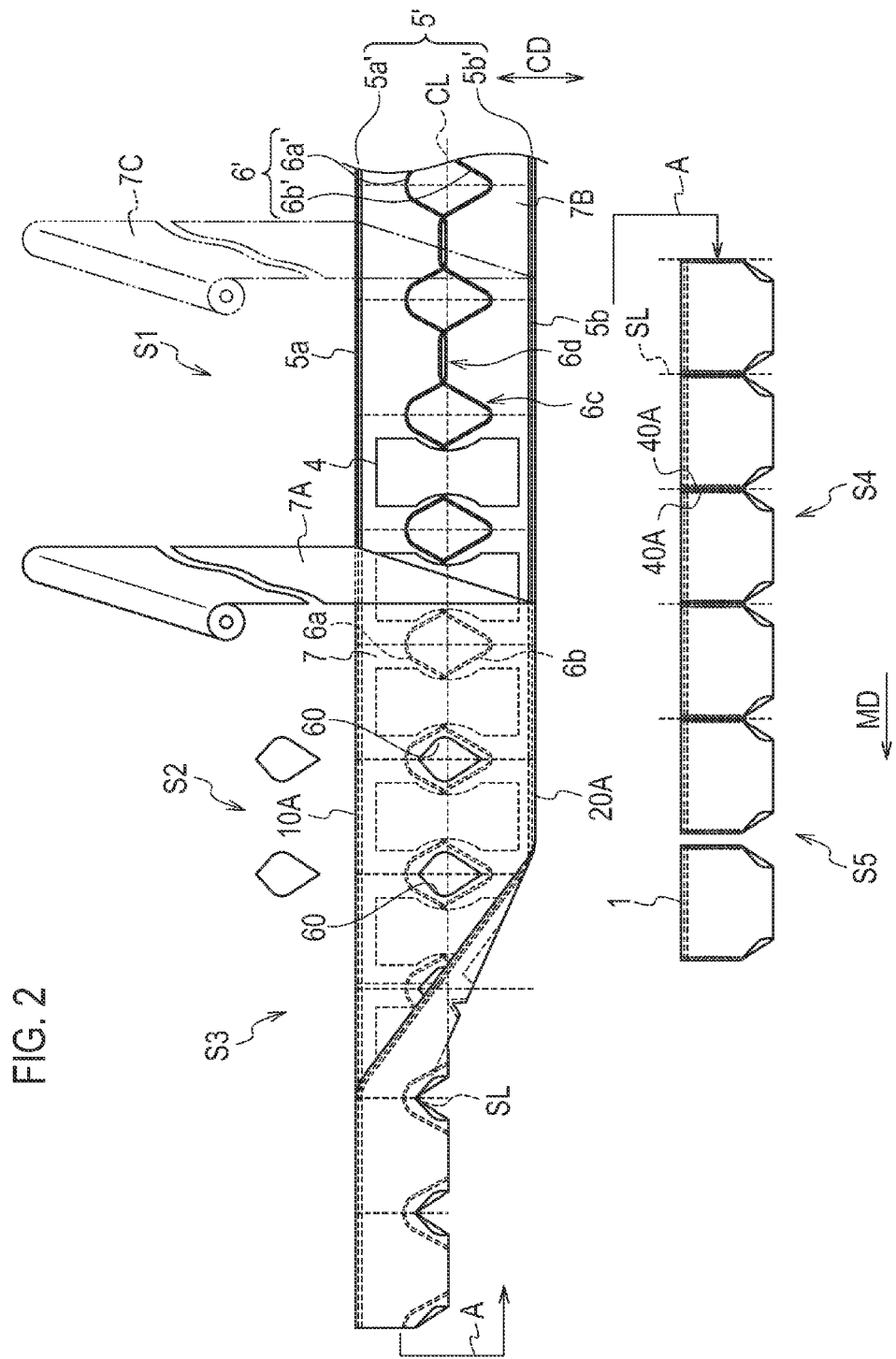
FIG. 2 is a diagram for explaining a part of a method for manufacturing the absorbent article according to the present embodiment.

The front waistline region 10 and the rear waistline region 20 have elasticity in a conveyance direction MD of a first web 7A configuring the topsheet 2 and a second web 7B configuring the backsheet 3 (see FIG. 2). For example, the front waistline region 10 and the rear waistline region 20 may have elasticity in the conveyance direction MD due to the provision of waist gathers 5, or may have elasticity in the conveyance direction MD due to the formation of the front waistline region 10 and the rear waistline region 20 by a sheet having elasticity.

The crotch region 30 is provided between the front waistline region 10 and the rear waistline region 20. Leg gathers 6 made of thread-shaped or band-shaped rubber having elasticity are provided on both sides of the crotch region 30. The leg gathers 6 are configured from front leg gathers 6a positioned the front waistline region 10 side and rear leg gathers 6b positioned the rear waistline region 20 side. A leg hole opening region 60 is formed between the front leg gathers 6a and the rear leg gathers 6b, and on both sides of the crotch region 30.

The crotch region 30 has elasticity in the cross direction CD that crosses the conveyance direction MD. For example, the crotch region 30 may have elasticity in the cross direction CD due to the provision of the leg gathers 6, or may have elasticity in the cross direction CD due to the formation of the crotch region 30 by a sheet having elasticity.

(2) Method for Manufacturing Absorbent Article

Next, a configuration of a method for manufacturing the absorbent article according to the present embodiment is explained with reference to drawings. FIG. 2 is a diagram for explaining a part of the method for manufacturing the absorbent article according to the present embodiment.

As illustrated in FIG. 2, the method for manufacturing the absorbent article includes at least a component loading step, a leg hole forming step, a folding step, a joining step, and a cutting step. A step of conveying the liquid-permeable first web 7A configuring the topsheet 2, the liquid-impermeable second web 7B configuring the backsheet 3, and a third web 7C made of materials such as the same material as that of the second web 7B and configuring the backsheet 3 in a conveyance direction MD by a conveyor (for example, a belt conveyor), which is not shown in the figure, is included between each step.

(2-1) Component Loading Step

In a component loading step S1, the components configuring the absorbent article 1, such as the elastic members, the third web 7C, the waterproof sheet (not shown in the figure), and the absorber 4 are loaded on the second web 7B.

Specifically, firstly, the elastic members 5' configuring the waist gathers 5 in an extended state are loaded in a linear state at a position corresponding to the front waistline region 10 and the rear waistline region 20 in the second web 7B. That is, an elastic member 5a' configuring a front waist gather 5a and an elastic member 5b' configuring a rear waist gather 5b are loaded at the position corresponding to the front waistline region 10 and the rear waistline region 20 in the second web 7B. Thus, waist gathers 5 (front waist gathers 5a and rear waist gathers 5b) are formed at the position corresponding to the front waistline region 10 and the rear waistline region 20 in the second web 7B.

Secondly, the third web 7C is loaded on the second web 7B. At this time, the elastic members 6' configuring the leg gathers 6 in an extended state are arranged, while are swung in the cross direction CD in a predetermined cycle, at the position corresponding to the crotch region 30 in the second web 7B and the third web 7C. Thus, the elastic members 6' are sandwiched between the second web 7B and the third web 7C, and form the leg gathers 6 (front leg gathers 6a and rear leg gathers 6b).

Note that the second web 7B and the third web 7C that sandwich the elastic members 6' are pressed by an upper press roll 130A and a lower press roll 130B (see FIG. 3) described later.

An elastic member 6a' that configures a front leg gather 6a and an elastic member 6b' that configures a rear leg gather 6b form a large annular portion 6c and a small annular portion 6d whose size in the cross direction CD is smaller than that of the large annular portion 6c.

As described above, after arranging the elastic member 6' in the second web 7B and the third web 7C, the second web 7B and the third web 7C are pressed by the upper press roll 130A and the lower press roll 130B. At this time, unless the planned position at which the small annular portion 6d is formed is pressed, the elastic members 6' are not fixed on to the web at the planned position. Because the elastic members 6' are arranged in an extended state, the elastic members constrict at the locations where it is not fixed on to the web, and takes an almost linear shape from the predetermined arrangement shape. Thus, the small annular portion 6d is formed.

When an adhesive is not applied at the planned position is same way. Because the elastic members 6' are not fixed on to the web at the planned position where an adhesive is not applied, the small annular portion 6d can be formed in the same way.

Thirdly, a waterproof sheet (not shown in the figure) and the absorber 4 are loaded on to the second web 7B and the third web 7C while the elastic member 6' is sandwiched in between such that the waterproof sheet and the absorber 4 are aligned at a fixed interval in the conveyance direction MD. Note that the waterproof sheet may be loaded on the second web 7B and the third web 7C by joining beforehand with the absorber 4, or may be loaded on the second web 7B and the third web 7C separately from the absorber 4.

Fourthly, the first web 7A configuring the topsheet 2 is superposed on to the second web 7B and the third web 7C on which the components configuring the absorbent article 1 have been loaded.

Note that the component loading step S1 need not necessarily be performed in the order of first to fourth, and can be changed appropriately.

(2-2) Leg Hole Forming Step

In a leg hole forming step S2, after the component loading step S1, the leg hole 1 opening region 60 (the so-called leg hole) is formed at the second web 7B and the first web 7A (hereinafter, the composite web 7) between which the components are held, by cutting out the inner periphery of the large annular portion 6c.

(2-3) Folding Step

In a folding step S3, after the leg hole forming step S2, the composite web 7 is folded into two along the center line CL through the center in the cross direction CD of the composite web 7 and toward the conveyance direction MD. In other words, a side edge 10A of the composite web 7 corresponding to the front waistline region 10, and a side edge 20A of the composite web 7 corresponding to the rear waistline region 20 overlap in a matching state.

(2-4) Joining Step

In a joining step S4, after the folding step S3, a predetermined region 40A corresponding to the joint portion 40 of the absorbent article 1 is joined with an ultrasonic treatment and a heat treatment. Note that the predetermined region 40A shows both sides, in the conveyance direction MD, of a virtual line SL showing the estimated cutting position extending in the cross direction CD.

(2-5) Cutting Step

In a cutting step S5, after the joining step S4, the composite web 7 on to which the predetermined region 40A is joined is cut along the virtual line SL. The absorbent article 1 is thus formed.

(3) Configuration of the Elastic Member Mounting Device

Figure 3:
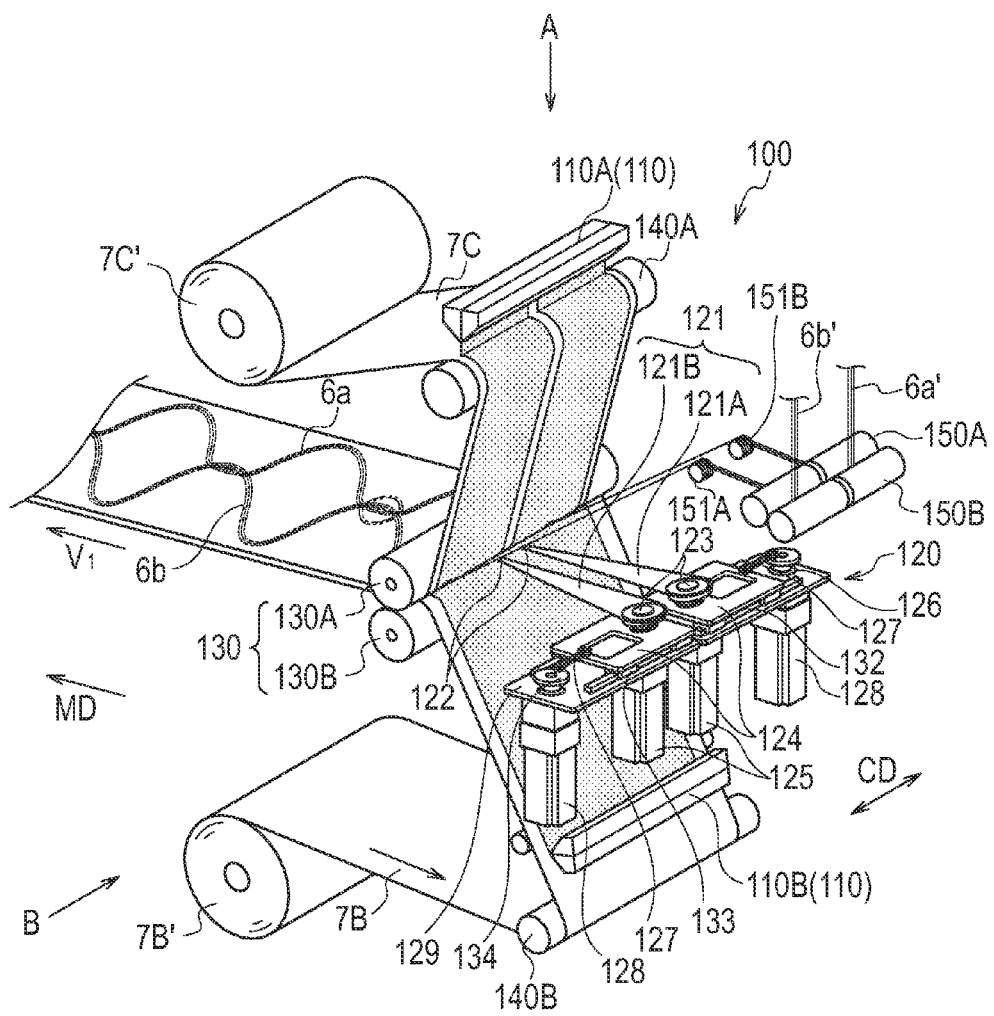
FIG. 3 is a perspective view illustrating an elastic member mounting device according to the present embodiment.
Figure 4:
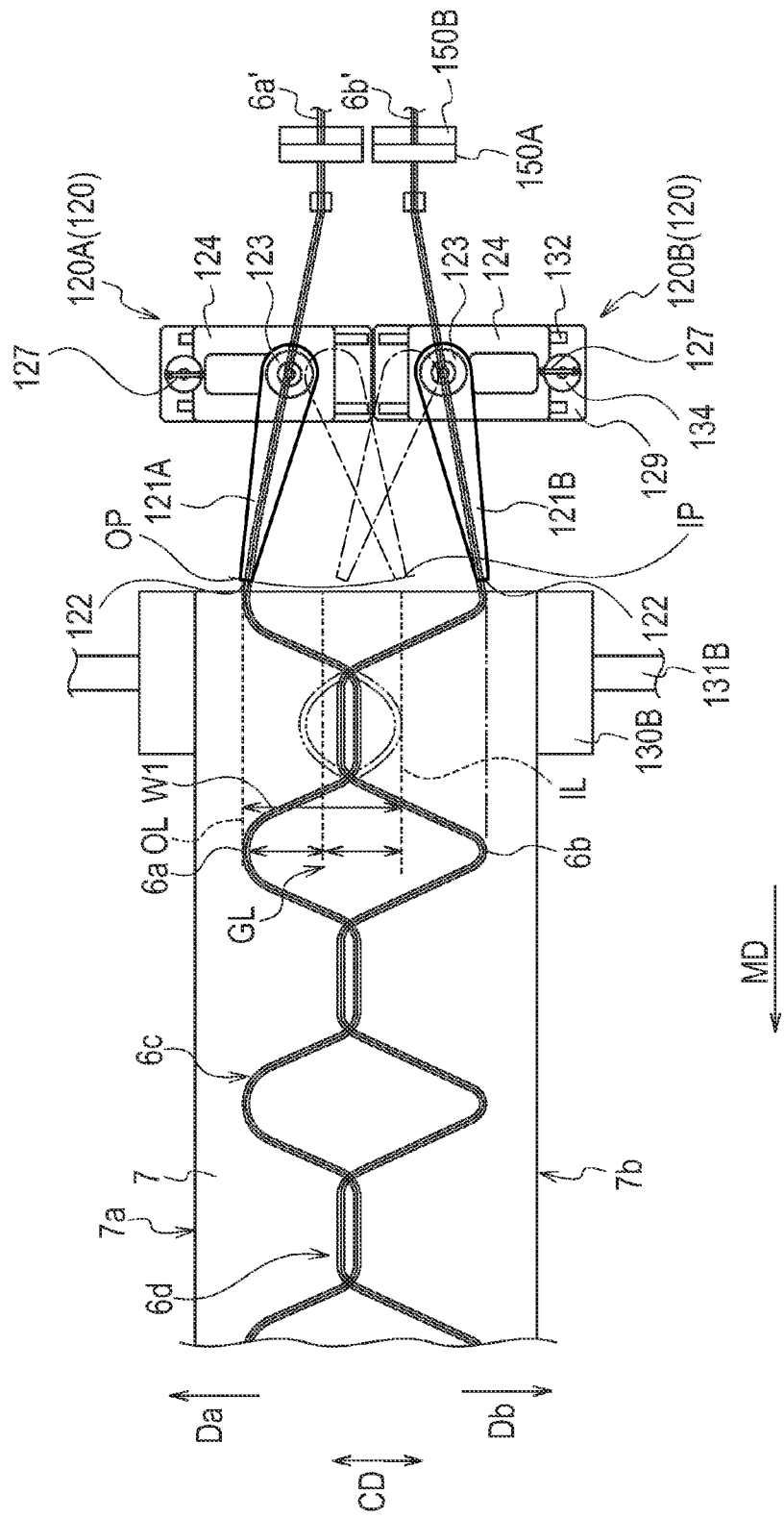
FIG. 4 is a top view (view on arrow A of FIG. 3) illustrating the elastic member mounting device according to the present embodiment.

Next, a configuration of an elastic member mounting device 100 used in the aforementioned component loading step S1 is explained with reference to drawings. The elastic member mounting device 100 configures a part of the apparatus for manufacturing the absorbent article. FIG. 3 is a perspective view showing the elastic member mounting device 100 according to the present embodiment. FIG. 4 is a top view (view on arrow A of FIG. 3) showing the elastic member mounting device 100 according to the present embodiment.

As shown in FIG. 3 and FIG. 4, the elastic member mounting device 100 arranges the elastic member 6' configuring the leg gathers 6 between the second web 7B and the third web 7C while swinging the elastic member 6' in the cross direction CD in a predetermined cycle. That is, the elastic member mounting device 100 forms the leg gathers 6 (the front leg gather 6a and the rear leg gather 6b) by arranging the elastic member 6' in a curved shape between the second web 7B and the third web 7C.

The elastic member mounting device 100 includes at least a web feeding mechanism (not shown in the figure), a gathers feeding mechanism (not shown in the figure), an adhesive application mechanism 110, a guide mechanism that guides the elastic members, and a press roll mechanism 130.

(3-1) Web Feeding Mechanism

The web feeding mechanism sequentially feeds a web from an original fabric. Specifically, the web feeding mechanism includes an upper web feeding mechanism for sequentially feeding the third web 7C from a third web original fabric 7C', and a lower web feeding mechanism for sequentially feeding the second web 7B from a second web original fabric 7B'.

The upper web feeding mechanism and the lower web feeding mechanism sequentially feed the second web 7B and the third web 7C, via rollers 140A and 140B that rotate around a rotational axis (not shown in the figure) running along the cross direction CD, toward the press roll mechanism 130.

(3-2) Gathers Feeding Mechanism

The gathers feeding mechanism sequentially feeds the elastic member 6' configuring the leg gathers 6 from an original fabric. Specifically, the gathers feeding mechanism includes front gathers feeding mechanism for sequentially feeding the elastic member 6a' configuring the front leg gather 6a from an original fabric (not shown in the figure) and a rear gathers feeding mechanism for sequentially feeding the elastic member 6b' configuring the rear leg gather 6b from an original fabric (not shown in the figure).

The front gathers feeding mechanism and the rear gathers feeding mechanism sequentially feed the leg gathers 6 toward the press roll mechanism 130 via feed rolls 150A and 150B that rotate around a rotational axis (not shown in the figure) running along the cross direction CD, and via splitting rolls 151A and 151B that split the elastic member 6a' and the elastic member 6b'.

(3-3) Adhesive Application Mechanism

The adhesive application mechanism 110 is a spray-type device for applying an adhesive (for example, a hot-melt adhesive) on the web. Specifically, the adhesive application mechanism 110 includes an upper adhesive application mechanism 110A for applying an adhesive on the third web 7C and a lower adhesive application mechanism 110B for applying an adhesive on the second web 7B.

Note that the upper adhesive application mechanism 110A is used to apply the adhesive on a surface excluding the central portion of the third web 7C. On the other hand, the lower adhesive application mechanism 110B is used to apply the adhesive on an entire surface of the second web 7B.

(3-4) Guide Mechanism

The guide mechanism swings the elastic member 6' configuring the leg gathers 6 in the cross direction CD in a predetermined cycle, and arranges the elastic member 6' on the web. Specifically, the guide mechanism is configured by a guide member 120 having a first guide member 120A that arranges the elastic member 6a' configuring the front leg gather 6a on a web, and a second guide member 120B that arranges the elastic member 6b' configuring the rear leg gather 6b. It must be noted that the first guide member 120A and the second guide member 120B basically have the same configuration. The details of the guide member 120 will be described later.

(3-5) Press Roll Mechanism

The press roll mechanism 130 presses the second web 7B and the third web 7C while the elastic member 6' is sandwiched between the second web 7B and the third web 7C. Specifically, the press roll mechanism 130 includes an upper press roll 130A that is in contact with the third web 7C, and a lower press roll 130B that is in contact with the second web 7B.

The upper press roll 130A rotates around a rotational axis along the cross direction CD. Similarly, the lower press roll 130B rotates around a rotational axis along the cross direction CD. The elastic member 6' is led by the guide member 120 to the location where the upper press roll 130A and the lower press roll 130B are the closest. The point where the upper press roll 130A and the lower press roll 130B contact with the elastic member 6' at the location where the upper press roll 130A and the lower press roll 130B are the closest is the contact point.

(4) Operation of the Elastic Member Mounting Device

Next, an operation of the elastic member mounting device 100 according to the present embodiment is explained based on FIG. 3 and FIG. 4. The third web 7C is fed from the third web original fabric 7C' by the upper web feeding mechanism, and the direction of movement is changed by a roller 140A. To the surface of which the third web 7C in which the direction of movement is changed faces the second web 7B, an adhesive is applied by the upper adhesive application mechanism 110A. At that time, the upper adhesive application mechanism 110A applies the adhesive on a surface excluding the central portion of the third web 7C. The third web 7C on which the adhesive is applied is supplied between the upper press roll 130A and the lower press roll 130B from above.

Similarly, the second web 7B is fed from the second web original fabric 7B' by the lower web feeding mechanism and the direction of movement is changed by a roller 140B. To the surface of which the second web 7B in which the direction of movement is changed faces the third web 7C, an adhesive is applied by the lower adhesive application mechanism 110B. The second web 7B on which the adhesive is applied is supplied between the upper press roll 130A and the lower press roll 130B from below.

The elastic member 6a' is fed from an original fabric (not shown in the figure) by the front gathers feeding mechanism, and the direction of movement is turned by a feed roll 150A. The elastic member 6a' that is turned by the feed roll 150A is split by a splitting roll 151A. The split elastic member 6a' is moved in the cross direction CD in a predetermined cycle by the first guide member 120A. Therefore, the elastic member 6a' is arranged in a curved shape between the second web 7B and the third web 7C, and thus forms the front leg gather 6a.

Similarly, the elastic member 6b' is fed from an original fabric (not shown in the figure) by the rear gathers feeding mechanism, and the direction of movement is turned by a feed roll 150B. The elastic member 6b' that is turned by the feed roll 150B is split by a splitting roll 151B. The split elastic member 6b' is moved in the cross direction CD in a predetermined cycle by the second guide member 120B. Therefore, the elastic member 6b' is arranged in a curved shape between the second web 7B and the third web 7C, and thus forms the rear leg gather 6b.

The elastic member 6a' and the elastic member 6b' are pressed by the upper press roll 130A and the lower press roll 130B while being sandwiched between the second web 7B on which an adhesive has been applied and the third web 7C. Therefore, the elastic member 6a' and the elastic member 6b' are adhered between the second web 7B and the third web 7C while being swung by the guide member 120, and thus, the aforementioned large annular portion 6c is formed. On the other hand, even though the elastic member 6a' and the elastic member 6b' are arranged between the second web 7B and the third web 7C, but because the adhesive is not applied in the central portion of the third web 7C, a restoring force occurs in the elastic member 6a' and the elastic member 6b' and the small annular portion 6d is formed.

(5) Configuration of Guide Member

Next, a configuration of the guide member 120, which is a characteristic of the present invention, is explained with reference to FIG. 3 through FIG. 6. The guide member 120 includes a pair of arm members 121, a pair of first drive members 125, and a pair of second drive members 128. The arm member 121 guides the elastic member 6' to a predetermined position in the cross direction CD between the second web 7B and the third web 7C.

The arm members 121 include a first arm member 121A that guides the elastic member 6a' configuring the front leg gather 6a, and a second arm member 121B that guides the elastic member 6b' configuring the rear leg gather 6b. Each of the pair of arm members 121 includes a tip portion 122, which is the feeding position of the elastic member 6', and a base portion 123 arranged away from the tip portion 122. The arm members 121 are configured to swing about the base portion 123 as a rotational axis.

The arm members 121 form a tapered plate shape from the base portion 123 to the tip portion 122. The arm members 121 are preferably arranged horizontally. The arm members 121 are formed by using a metal plate. For example, the arm members 121 are formed by using a stainless steel plate.

It must be noted that the length of the first arm member 121A and the second arm member 121B may be configured to be different, or the length of the first arm member 121A and the second arm member 121B may be configured to be the same. The length of the arm member 121 is the length from the tip portion 122 of the arm member 121 up to the base portion 123, which is the rotational axis of the arm member 121.

The first drive members 125 swing the arm members 121 about the base portion 123 of the arm members 121 as the rotational axis. The first drive members 125 are configured by a servo motor that is operated by a controller in which a program that assigns a predetermined expansion magnitude to the elastic member 6' according to the conveyance speed of the composite web 7, and with which the elastic member 6' can be arranged in a desired layout is input.

It must be noted that the program that operates the first drive member 125 of the first arm member 121A is different from the program that operates the first drive member 125 of the second arm member 121B. That is, the predetermined expansion magnitude and layout of the front leg gather 6a is different from the predetermined expansion magnitude and layout of the rear leg gather 6b.

Each of the pair of first drive members 125 includes a rotational axis 126 that is directly connected to the rotational axis of the first arm member 121A and the second arm member 121B. The first drive members 125 swing the first arm member 121A and the second arm member 121B about the base portion 123, via the rotational axis 126. The arm members 121 and the first drive members 125 are joined with a bracket 124. The bracket 124 includes a guide engagement unit 133 that is engaged with a guide rail 132 fixed on a base plate 129, and is configured to be able to perform a sliding movement in the cross direction CD along the guide rail 132.

The second drive members 128 perform a back and forth movement of the arm members 121 and the first drive members 125 in the cross direction CD, via the bracket 124. The second drive members 128 are motors providing a rotating drive. A crank disc 134 that is directly connected to the rotational axis of the second drive members 128 is connected to the bracket 124 via a connecting rod 127. The rotation motion caused by the second drive members 128 is converted to a back and forth sliding movement via the crank disc 134 and the connecting rod. Thus, the bracket 124 performs a sliding movement in the cross direction CD due to the rotation of the second drive members 128. The first drive members 125 and the arm members 121 perform a back and forth movement in the cross direction CD along with the bracket 124.

(6) Operation of Guide Member

Depending on the swinging manner of the arm members 121, the second drive members 128 control the arm members to perform a sliding movement in the cross direction CD. Next, the operation of the guide member 120 will be explained in detail based on FIG. 4 through FIG. 6. The first guide member 120A and the second guide member 120B are controlled in the same manner, therefore the explanation is provided using the first guide member 120A and the elastic member 6a' arranged by the first guide member 120A.

In FIG. 4, the first arm member 121A of the first guide member 120A has a tip portion 122 that feeds the elastic member 6a' on the web, and by alternately moving the tip portion 122 in a first direction Da from the central portion of the second web 7B (the third web 7C) that is conveyed in the conveyance direction MD toward a first end 7a in the cross direction CD, and in a second direction Db from the central portion of the second web 7B (the third web 7C) toward a second end 7b, which is the end opposite the first end, by the arm members 121 that guide the elastic member 6a', the elastic member 6a' is brought in contact between the second web 7B and the third web 7C and arranged in a gather waveform (a predetermined waveform).

Figure 5:
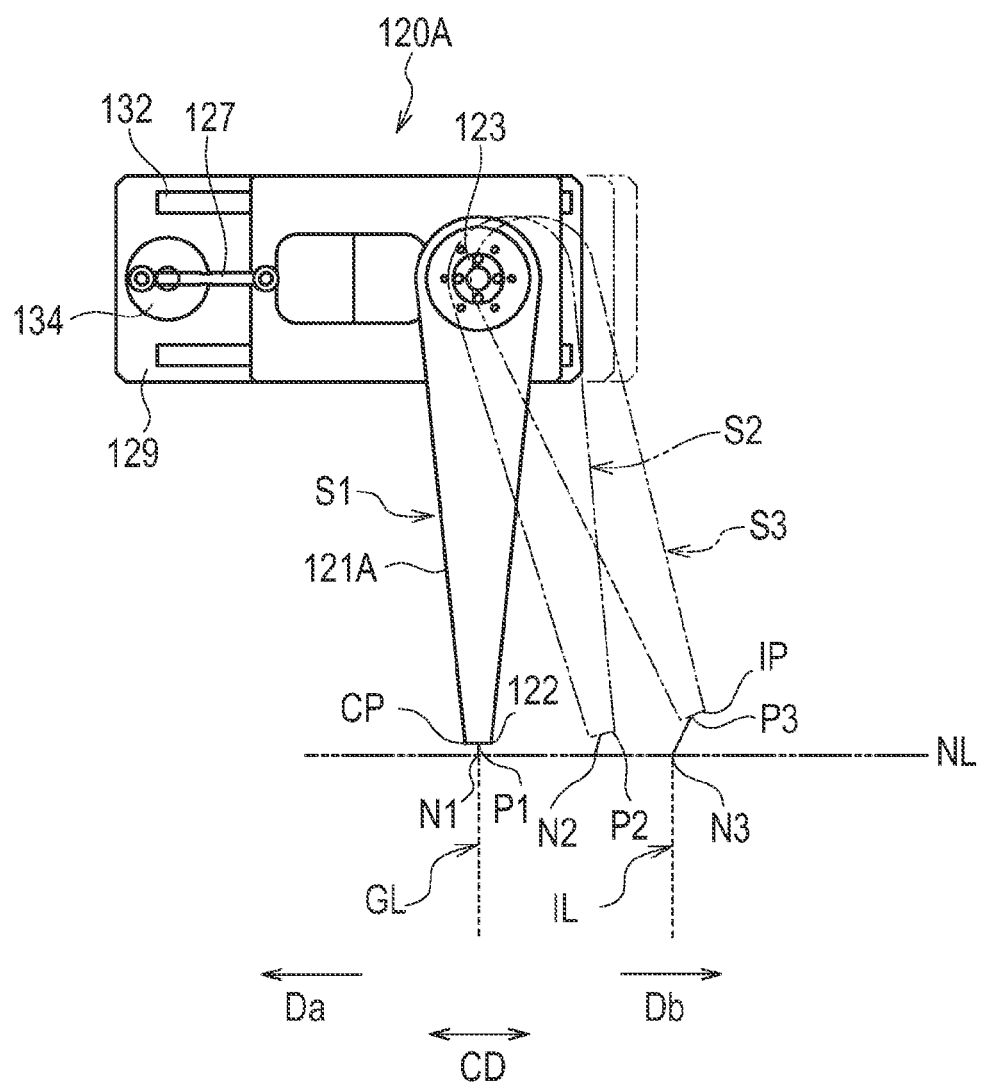
FIG. 5 is a schematic view illustrating a state of operation of a guide member in the top view (view on arrow A of FIG. 3) illustrated in FIG. 4.

FIG. 5 is a schematic view illustrating an operation of the first guide member 120A in the view on arrow A of FIG. 3. In FIG. 5, NL virtually illustrates the position of the contact point where the web 7 and the elastic member 6' come in contact on the upper press roll 130A and the lower press roll 130B. The tip portion 122 of the first arm member 121A swings in the cross direction CD within a predetermined range (W1 shown in FIG. 4) in the cross direction CD. A waveform center line GL represents the center line in the cross direction CD of the gather waveform. An outer end line OL represents the outer end in the cross direction CD of the gather waveform. An inner end line IL represents the inner end in the cross direction CD of the gather waveform.

The tip portion 122 of the first arm member 121A is configured to swing between a center position CP that is the center of a predetermined range W1, and an outer end position OP and inner end position IP that form both ends in the outer sides of the predetermined range W1, in the cross direction CD. When the first arm member 121A is at the center position CP, the elastic member 6' is arranged on the waveform center line GL. When the first arm member 121A is at the outer end position OP, the elastic member 6' is arranged on the outer end line OL. When the first arm member 121A is at the inner end position IP, the elastic member 6' is arranged on the inner end line IL. It must be noted that the center position is the position at the center of the movement trajectory of the tip portion 122, in other word.

FIG. 5 is a diagram that schematically illustrates the operation when the first arm member 121A moves from the center position CP toward the inner end position IP. S1 indicates the state when the tip portion 122 of the first arm member 121A is at the center position CP, and a contact point N1 of the elastic member 6' is arranged on the waveform center line GL. At this time, a forward position (that is, the feeding position P1) of the elastic members at the tip portion 122 of the first arm member 121A matches the contact point N1 in the cross direction CD.

S2 indicates the state when the tip portion 122 of the first arm member 121A is at an intermediate position between the center position CP and the inner end position IP. A state S2 comes into existence when in a state S1, the first drive members 125 swing the first arm member 121A toward the Db direction, and the second drive members 128 perform a sliding movement of the first arm member 121A and the like in the Db direction via the bracket 124. At this time, the feeding position P2 does not match the contact point N2 in the cross direction CD, is displaced.

S3 indicates the state when the tip portion 122 of the first arm member 121A is at the inner end position IP. A state S3 comes into existence when in the state S2, the first drive members 125 swing the first arm member 121A toward the Db direction, and the second drive members 128 move the first arm member 121A in the Db direction via the bracket 124. At this time, the length of displacement of the feeding position P3 and a contact point N3 in the cross direction CD becomes longer than that in the state S2.

The second drive members 128 are configured to move the arm members 121 and the first drive members 125 toward the outer end position OP and the inner end position IP when the tip portion 122 moves from the center position CP toward the outer end position OP and the inner end position IP, and to move the arm members 121 and the first drive members 125 toward the outer end position OP and the inner end position IP when the tip portion 122 moves from the outer end position OP and the inner end position IP toward the center position CP.

When the tip portion 122 of the arm members 121 is at the outer end position OP and the inner end position IP, the second drive members 128 perform a sliding movement of the arm members so that the arm members 121 and the first drive members 125 are positioned at the outermost sides in the cross direction CD. The second drive members 128 perform a sliding movement of the arm members 121 and the first drive members 125 according to the swinging cycle of the arm members 121. Specifically, for example, by configuring the second drive members by a servo motor and matching the rotation cycle of the servo motor with the cycle of the servo motor configuring the first drive members, the swinging cycle of the arm members can be matched with the sliding cycle. The servo motor configuring the second drive member may be configured to drive at a constant speed, or may be configured such that the speed changes.

Furthermore, the swinging cycle of the arm members can be matched with the sliding cycle, by configuring the second drive members by an induction motor, and matching the sliding cycle of the arm members with the cycle of the servo motor configuring the first drive members by using an inverter that changes the frequency.

As illustrated in FIG. 5, if the distance between feeding position and the contact point in the conveyance direction MD is compared, the distance is longer in the state S3 than the state S1. The rotation angle of the arm members becomes larger at the ends in the cross direction of the movement trajectory of the arm members, and as a result, the distance between the feeding position and the contact point becomes longer, and the length of displacement of the feeding position and the contact point in the cross direction becomes longer.

However, as the arm members perform a sliding movement in the cross direction by the second drive members 128, the position of the contact point of the elastic members and the web can be changed not only by the movement caused by swinging of the arm members 121, but also by the back and forth sliding movement of the arm members 121 in the cross direction. Therefore, as compared to the case when the elastic members are swung in the cross direction only by the movement caused by swinging of the arm members, the rotation angle of the arm members can be reduced, and the distance between the feeding position and the contact point in the conveyance direction MD can be shortened. Thus, the length of displacement of the feeding position and the contact point in the cross direction can be shortened.

Figure 6:
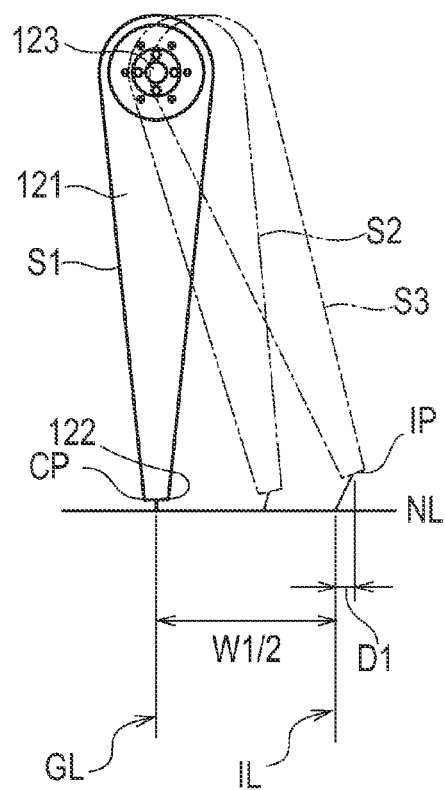
FIG. 6 is a schematic view that schematically illustrates a state of operation of the arm members.
Figure 6:
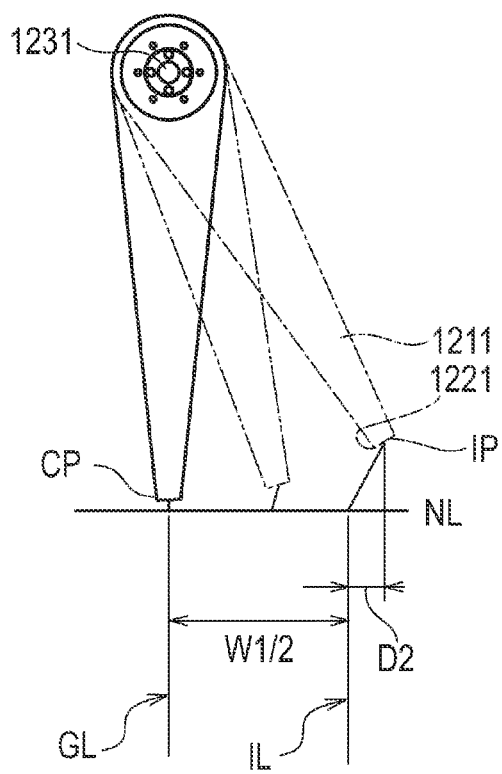

FIG. 6 is a schematic view of the comparison between the operation of the arm member 1211 that is driven only by the first drive members 125, and the operation of the arm member 121 that is driven by the first drive members 125 and the second drive members 128. FIG. 6(a) is a diagram illustrating the operation of the arm member 121 that is driven by the first drive members 125 and the second drive members 128. FIG. 6(b) is a diagram illustrating the operation of the arm member 1211 that is driven only by the first drive members.

As illustrated in FIG. 6(b), when the arm members 1211 is driven only by the first elastic members, the arm member 1211 does not perform a back and forth movement in the cross direction CD. The arm member 1211 leads the elastic members in the cross direction CD only by swinging about the base portion 1231 as the center. As the arm member 1211 approaches the inner end position IP, the inclination of the arm members 121 increases, and the amount of movement of the tip portion 1221 in the cross direction CD reduces. Furthermore, the distance between the feeding position and the contact point becomes longer at the inner end position IP than at the center position CP. If the distance between the feeding position and the contact point becomes longer, a length D2 of displacement of the feeding position and the contact point in the cross direction CD becomes longer.

In view of the length of displacement of the feeding position and the contact point, when the tip portion 1221 of the arm member 1211 is positioned near the end in the cross direction, the tip portion 1221 of the arm member 1211 needs to be moved from the contact point where the elastic members must be arranged up to the outer sides in the cross direction. Therefore, the amount of movement of the tip portion 1221 of the arm members 1211 becomes larger in the case when the elastic members are led within the range from the intermediate position to the inner end position IP than the case when the elastic members are led within the range from the center position CP to the intermediate position. When the tip portion 1221 of the arm member 1211 is positioned near an end in the cross direction, the acceleration of the arm member 1211 increases.

On the other hand, as illustrated in FIG. 6(a), when the arm member 121 performs a back and forth sliding movement in the cross direction CD, the elastic members are led in the cross direction CD by the swinging of the arm member 121 and the siding movement of the arm member 121, and therefore, as compared to the configuration illustrated in FIG. 6(b), the angle of inclination of the arm member 121 at the inner end position IP can be reduced, and a length D1 of displacement of the feeding position and the contact point in the cross direction CD can be shortened.

By performing a sliding movement of the arm member 121 in the cross direction CD, the amount of movement of the tip portion 122 of the arm member 121 in the cross direction CD becomes the amount of movement obtained by combining the movement element in the cross direction CD in the arc-shaped movement trajectory based on swinging of the arm member 121, and the movement element in the cross direction based on the back and forth movement of the arm member 121. Thus, the rotation angle of the arm member 121 at the time of leading the elastic members can be reduced across the same width (W1/2 in FIG. 6) in the cross direction CD, and the distance between the tip portion 122 and the contact point can be shortened.

As a result of such a configuration, the length of displacement of the feeding position and the contact point in the cross direction CD is shortened, and the inner end position IP of the arm member 121 can be brought closer to the center position CP. The amount of movement of the arm member 121 is reduced, and the damage of the arm member 121 caused by an increase in acceleration of the arm member 121 can be prevented. Furthermore, due to a reduction in the amount of movement of the arm member 121, the length of the arm members can be reduced.

(7) Other Embodiments

So far, the present invention is disclosed through the above embodiments. However, it should not be interpreted that the statements and drawings constituting a part of the present disclosure limit the present invention. From the present disclosure, various alternative embodiments, examples, and operational technologies will become apparent to those skilled in the art.

For example, the embodiment of the present invention can be modified as follows. Specifically, a speed reducer may be provided in the first drive members and the second drive members. By providing a speed reducer, for example, the swinging speed of the arm members and the speed of the sliding movement of the bracket can be reduced more than the rotation speed of the first drive members and the second drive members. Thus, the moment of inertia of the arm members, etc. on the first drive members and the second drive members reduces, because of which the arm members can be strengthened along with an increase in weight, and the damage of the arm members can surely be reduced. Furthermore, the first drive members and the second drive members can be rotated at the desired speed, which enables an increase in the production speed. Particularly, because the second drive members drive the bracket, the first drive members, and the arm members, the moment of inertia on the second drive members becomes large. Therefore, it is desired to provide a speed reducer in combination with the second drive members.

Furthermore, in the present embodiment, a sliding drive is provided to the arm members via the crank disc and the connecting rod due to the rotation of the motor configuring the second drive members, however, for example, a screw hole may be formed in the bracket along the cross direction, a ball screw may be inserted in the screw hole, and a sliding drive is provided to the arm members by the rotation of the ball screw.

In addition, in the present embodiment, the arm members are configured to be moved in a sliding in the cross direction CD by the second drive members due to swinging of the arm members by the first drive members, however, the first drive members and the second drive members may not necessarily provide a drive at the same time. For example, when the tip portion of the arm members moves from the center position toward an end position, then rather than performing a sliding movement of the arm members in the cross direction upon moving within a predetermined range from the center position, the arm members may be configured to move in the cross direction upon moving up to an end position beyond the predetermined range. Even according to such a configuration, the distance between the tip portion of the arm member and the contact point can be brought closer when the arm member is at the end position, and the length of displacement at the end position can be shortened.

Furthermore, in the present embodiment, the arm members are configured to perform a sliding movement in the cross direction when the tip portion of the arm members moves from the center position toward the inner end position, and to perform a sliding movement in the cross direction when the tip portion of the arm members moves from the center position toward the outer end position, however, the arm members may be configured to perform a sliding movement in the cross direction only when the tip portion moves toward either one of the inner end position and the outer end position.

The method for manufacturing the absorbent article and the apparatus for manufacturing the absorbent article is not restricted to the absorbent article 1 (the so-called disposable diaper) having the front waistline region 10, the rear waistline region 20, and the crotch region 30, but can be applied to various articles, such as disposable gowns in the medical field, or disposable sportswear, or the like. Furthermore, it was explained that the elastic members of the components of the absorbent article 1 were formed of thread-shaped rubber having elasticity, but the elastic members are not restricted thereto, and may be formed of plain rubber and sheet-like rubber, or the like. Furthermore, the elastic members may not necessarily be formed of rubber. For example, the elastic members may be fibers of polyester or polyurethane having resilience and elasticity. Other elastic fibers may also be used. A plurality of such fibers can also be twisted together and used.

Furthermore, in the present embodiment, the waveform in which the elastic members are arranged by the first guide members 120A, and the waveform in which the elastic members are arranged by the second guide members 120B may be different or may be the same waveform.

In the embodiment according to the present invention, the first guide member 120A and the second guide member 120B are arranged such that the movable region of the arm member 121 is partially overlapping, however, the first guide member 120A and the second guide member 120B may be arranged at a mutually non-overlapping position. The interval between the first guide member 120A and the second guide member 120B in the web cross direction can be adjusted appropriately according to the product shape of the absorbent article 1 (the so-called disposable diaper). For example, the front leg gather 6a and the rear leg gather 6b may be conveyed in a state in which a predetermined interval is present mutually.

Furthermore, it was explained that the program that operated the first drive member 125 of the first guide member 120A was different from the program that operated the second drive member 128 of the second guide member 120B, however, this case is not restricted thereto, and the program may be the same as the program that operates the first drive member of the second guide member 120B. That is, the predetermined expansion magnitude and layout of the front leg gather 6a may be the same as the predetermined expansion magnitude and layout of the rear leg gather 6b.

In the present embodiment, the guide member 120 is configured to lead the elastic members in the cross direction by the arm member 121 that swings about the base portion 123, however, the configuration is not restricted to one in which the arm member 121 rotates about the base portion 123. For example, the guide member having a feeding position for feeding the elastic member 6a' may have a mechanism by which the specified movement range is covered by an arc-shaped slide rail, an arc-shaped rib, an arc-shaped cam groove and cam follower, and the like. In such a case, the applicable drive members include, for example, a timing belt, a linkage bar, and an arc-shaped linear servo.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2011-036995 (filed on Feb. 23, 2011) are incorporated in the present specification by reference.

INDUSTRIAL APPLICABILITY

According to the apparatus for manufacturing the absorbent article and the method for manufacturing the absorbent article of the present invention, as a back and forth movement of the arm members is performed in the cross direction while swinging the arm members in the cross direction, the position of the contact point of the elastic members and the web can be changed not only by the movement caused by swinging of the arm members, but also by the back and forth movement of the arm members in the cross direction. Therefore, as compared to the configuration in which the elastic members are swung in the cross direction only by the swinging of the arm members, the length of displacement of the tip portion at the end in the cross direction of the movement trajectory and the contact point in the cross direction can be shortened. Thus, it is possible to handle several sizes while reducing the amount of movement of the arm members in the cross direction, and preventing the damage of arm members caused by an increase in acceleration near the end in the cross direction.

REFERENCE SIGNS LIST

1: absorbent article
2: topsheet
3: backsheet
4: absorber
5: waist gather
5a: front waist gather
5b: rear waist gather
5', 5a', 5b': elastic member
6: leg gather
6a: front leg gather
6b: rear leg gather
6c: large annular portion
6d: small annular portion
6', 6a', 6b': elastic member
7: composite web
7A: first web
7B: second web
7B': second web original fabric
7C: third web
7C': third web original fabric
10: front waistline region
10A: side edge
20: rear waistline region
20A: side edge
30: crotch region
40: joint portion
40A: predetermined region
50: waist opening region
60: leg hole opening region
100: elastic member mounting device
110: adhesive application mechanism
110A: upper adhesive application mechanism
110B: lower adhesive application mechanism
120: guide member
120A: first guide member
120B: second guide member
121: arm member
121A: first arm member
121B: second arm member
122: tip portion
123: base portion
124: bracket
125: first drive member
126: rotational axis
127: connecting rod
128: second drive member
129: base plate
130: press roll mechanism
130A: upper press roll
130B: lower press roll
132: guide rail
133: guide engagement unit
134: crank disc
140A, 140B: backup roll
150A, 150B: feed roll
151A, 151B: splitting roll

The invention claimed is:

1. An apparatus for manufacturing an absorbent article having a front waistline region, a rear waistline region, and a crotch region positioned between the front waistline region and the rear waistline region, said apparatus comprising:
  a guide member configured to guide an elastic member fed on a web, said web configuring a component of the absorbent article and being conveyed in a continuous state in a conveyance direction,
  wherein the guide member comprises:
    an arm member having a tip portion that is a feeding position of the elastic member to the web;
    a base portion separated from the tip portion;
    a first motor configured to swing the arm member about the base portion of the arm member as a rotational axis; and
    a second motor configured to perform a back and forth movement of the arm member and the first motor along a cross direction that crosses the conveyance direction.

2. The apparatus according to claim 1, wherein
  the tip portion is configured to be swung between (i) a center position that is a center of a predetermined range in the cross direction and (ii) end positions that are the ends of the predetermined range in the cross direction, and
  the second motor is configured to move the arm member and the first motor toward the end positions when the tip portion moves from the center position toward the end positions.

3. The apparatus according to claim 2, wherein the second motor is configured to move the arm member and the first motor so that the position of the tip portion is at the outermost sides in the cross direction at the end positions.

4. The apparatus according to claim 1, wherein the first motor is a servo motor.

5. The apparatus according to claim 1, wherein the second motor is a servo motor.

6. A method of manufacturing an absorbent article having a front waistline region, a rear waistline region, and a crotch region positioned between the front waistline region and the rear waistline region, said method comprising:
  conveying a web configuring a component of the absorbent article, said web being conveyed in a continuous state in a conveyance direction; and
  arranging an elastic member on the web by
    swinging, by a first motor, an arm member having a tip portion, that is a feeding position of the elastic member to the web, within a predetermined range in a cross direction that crosses the conveyance direction,
    while performing, by a second motor, a back and forth movement of the arm member and the first motor in the cross direction.

* * * * *